United States Patent
Yoshino et al.

[11] Patent Number: 6,100,970
[45] Date of Patent: Aug. 8, 2000

[54] APPARATUS FOR INSPECTING SLIGHT DEFECTS ON A PHOTOMASK PATTERN

[75] Inventors: Hisakazu Yoshino; Akihiko Sekine, both of Tokyo; Toru Tojo, Kanagawa-ken; Mitsuo Tabata, Yokohama, all of Japan

[73] Assignees: Kabushiki Kaisha Topcon, Tokyo; Kabushiki Kaisha Toshiba, Kawasaki, both of Japan

[21] Appl. No.: 09/012,034

[22] Filed: Jan. 22, 1998

Related U.S. Application Data

[63] Continuation of application No. 08/748,898, Nov. 15, 1996.

[30] Foreign Application Priority Data

Nov. 17, 1995 [JP] Japan .................................. 7-299830

[51] Int. Cl.$^7$ .................................................. G01N 21/00
[52] U.S. Cl. ........................... 356/237; 356/388; 356/389
[58] Field of Search .................................... 356/237, 388, 356/389

[56] References Cited

U.S. PATENT DOCUMENTS 5,812,259  9/1998  Yoshino et al. ........................ 356/237

OTHER PUBLICATIONS

"Mask Defect Inspection Method by Database Comparison with 0.25–0.35 μm Sensitivity," Jpn. J. Appl. Phys. vol. 33 (1994) pp. 7156–7162.

*Primary Examiner*—Frank G. Font
*Assistant Examiner*—Reginald A. Ratcliff
*Attorney, Agent, or Firm*—Finnegan, Henderson, Farabow, Garrett & Dunner, L.L.P.

[57] ABSTRACT

A photomask defect inspection method is provided by which defects of pin holes with the diameter equal to or less than 0.35 μm can be detected with certainty. According to the inspection method, a pattern whose image is projected onto an imaging position by the use of illumination light (P1) for exposure consists of light transmitting portions (41) formed on a glass base (2) and light intercepting portions (42) which transmit part of the illumination light (P1) in such a way that a phase of the part of the illumination light (P1) passing through the light intercepting portions (42) is delayed with respect to a phase of the illumination light (P1) passing through the light transmitting portions (41). Slight detects in the photomask pattern are detected on the basis of a signal obtained by illuminating the pattern with inspection light having an inspection wavelength in which the transmittance (T) of the light intercepting portions (42) is defined in the following formula on the basis of a signal detection limit (Thr). When the signal detection limit (Thr) of an inspection circuit is calculated on the supposition that a signal level of the inspection light passing through the light transmitting portions (41) is equal to 1, the relational expression is $T \geq (Thr-0.01)^{1/1.8}$.

8 Claims, 17 Drawing Sheets

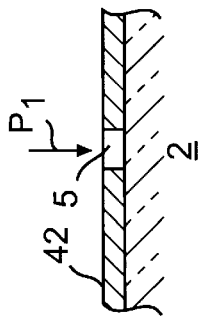 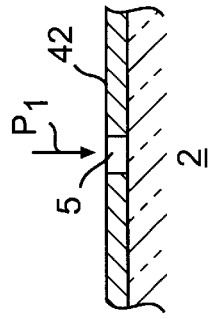 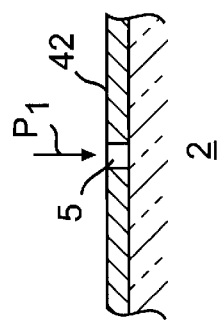 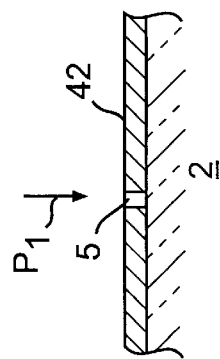
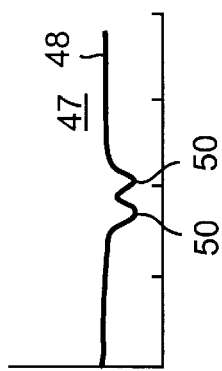 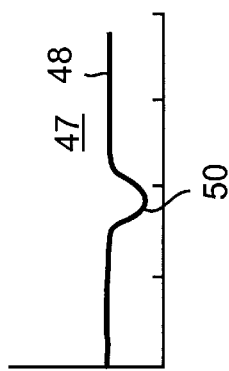 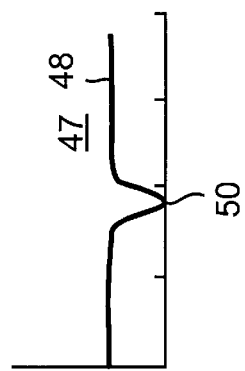 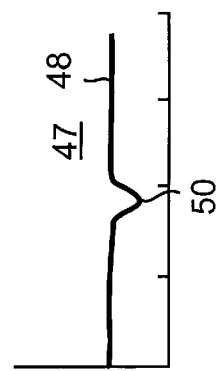
*FIG. 9(e)*  *FIG. 9(f)*  *FIG. 9(g)*  *FIG. 9(h)*

APPARATUS FOR INSPECTING SLIGHT DEFECTS ON A PHOTOMASK PATTERN

This is a continuation of application Ser. No. 08/748,898, filed Nov. 15, 1996.

BACKGROUND OF THE INVENTION

1. Field of the Invention

This invention relates to a method of and apparatus for inspecting slight defects in a photomask pattern.

2. Description of the Prior Art

A photomask 1 is used in the production of semiconductor integrated circuits. As shown in FIG. 1, the photomask 1 has a transparent base 2 on which, for example, two chips 3 each size of which is 10 mm×20 mm are formed. A circuit pattern 4 of a light intercepting film made of chromium (Cr) or the like is formed in the chips 3 in high density. The width of the circuit pattern 4 is, for example, 1 $\mu$m to 3 $\mu$m.

As shown enlargedly in FIG. 2, cases occur in which a part of the circuit pattern 4 has defects, such as a pin hole 5 or a projection 8, or has flaws, such as a crack 6 or a nick 7, or has foreign substances. If exposure is performed using such a defective photomask 1, a circuit pattern different from a predetermined circuit pattern 4 is formed on a semiconductor substrate (i.e., a wafer). In other fords, a semiconductor integrated circuit having pattern defects is formed. For this reason, an inspection of whether the formed photomask 1 has defects is beforehand undergone.

There are various kinds of methods of inspecting defects in the pattern of the photomask 1. Typically, an adjacent-pattern comparison method and a design-data comparison method are well known.

① Adjacent-Pattern Comparison Method

According to this method, two adjacent chips 3 are compared with each other and, when disagreements therebetween are found, it is judged that defects exist. This method is followed on the supposition that there is little probability that two adjacent chips 3 have the same defects in the same circuit patterns of the chips 3.

② Design-Data Comparison Method

According to this method, a circuit pattern is observed by a defect inspection apparatus, and the observed positions are compared with design-data corresponding to the positions.

These defect inspection methods ① and ② are properly used depending on purposes and uses.

FIG. 3 shows an example of the apparatus for inspecting defects in the pattern of the photomask 1. This inspection apparatus comprises a data processing system which includes a CPU 10, a magnetic disk unit 11, a magnetic tape unit 12, a floppy disk drive unit 13, a console CRT 14, a pattern monitor 15, a magnetic card unit 16, a miniprinter 17, an RS-232C adapter 18, and the like, a detective optical system which includes an autoloader control circuit 19, a table control circuit 20, an X-motor M1, a Y-motor M2, a θ-motor M3, an autofocus control circuit 21, a piezo-element 21a, a positioning circuit 22, a control circuit 22' of, for example, a laser length measuring system, a bit developing circuit 23, a pattern comparative inspection circuit such as a data comparison circuit 24, an autoloader 25 accommodating various kinds of photomasks 1, an illumination light source 26, an illumination field diaphragm 27, a condenser lens 28, an X-Y table 29, an objective lens 30, a photodiode array 31, a sensor circuit 32, and the like, and an observing scope which includes reflection mirrors 33, 34, an eyepiece 35, and the like (see a reference entitled "Mask Defect Inspection Method by Database Comparison with 0.25~0.35 $\mu$m Sensitivity", in Jpn. J. App. Phys, Vol 33(1994)7156). As shown in FIG. 4(a), the width of about 300 $\mu$m of the photomask 1 is observed by the photodiode array 31. The photodiode array 31 is disposed at a position where the circuit pattern is imaged. The photomask 1 is mounted on the X-Y table 29 and is illuminated with light from the illumination light source 26.

As shown in FIG. 4(b), the X-Y table 29 is transferred in the direction of arrow A1 at intervals of a predetermined pitch p. When measurements in the direction of arrow A1 are completed, the X-Y table 29 is transferred by the width W in the direction of arrow A2 and thereafter the X-Y table 29 is transferred at intervals of the predetermined pitch p in the direction of arrow A3. In the same manner, the X-Y table 29 is transferred successively in the directions of arrows A4, A5 . . . so as to inspect the whole range of the photomask 1.

The autofocus control circuit 21 drives autofocusably the objective lens 30 in the axial direction of the objective lens 30 so as to keep a distance between the objective lens 30 and the photodiode array 31 constant, and thereby accurate data can be obtained. The θ-motor M3 controls the X-Y table 29 to keep the photomask 1 parallel to the photodiode array 31.

Graphic data is beforehand stored as a circuit pattern in the magnetic disk unit 11. The circuit pattern 4 of the photomask 1 is projected enlargedly onto the photodiode array 31 by means of the objective lens 30, and an image of the circuit pattern 4 is formed on the photodiode array 31. The image of the circuit pattern 4 is photoelectrically transferred by the photodiode array 31 and is output to the sensor circuit 32 in the form of measured data. The measured data is converted from an analog signal to a digital signal and is input to a first input terminal of the data comparison circuit 24.

On the other hand, the graphic data is transmitted to the bit developing circuit 23 in accordance with a detected output of she positioning circuit 22. The graphic data is converted into a binary number system by means of the bit developing circuit 23 and is transmitted to a second input terminal of the data comparison circuit 24. The output of the positioning circuit 22 is input to a third input terminal of the data comparison circuit 24. The data comparison circuit 24 processes the binary bit pattern data through proper filters and thereby converts the binary bit pattern data into a multivalue system.

The reason why the binary bit pattern data is processed through the proper filters is that the measured data is being filtered by the resolution characteristic of the objective lens 30 and the aperture effect of the photodiode array 31.

Data in an observed position is compared with data in a corresponding position of pattern design data in accordance with a predetermined algorithm by means of the data comparison circuit 24. Thereby, disagreeing positions between the design data and the measured data are regarded as defects. In this type of pattern comparative defect inspection, in order to detect slight defects, the resolution of an optical system of an inspection means is enhanced, the algorithm for comparison is improved, or the processing of measured signals is improved.

However, the detection sensitivity to pattern defects largely depends upon the kinds of the defects. Especially, if a pattern defect of the circuit pattern 4 is a pin hole as shown in FIG. 2, it is difficult to detect it, and it is almost impossible to detect the defect of a pin-hole less then 0.35 $\mu$m in diameter.

In recent years, a phase shift type of photomask shown in FIG. 6(a) has been used instead of a conventional amplitude type shown in FIG. 5(a). In the amplitude type of photomask, illumination light P1 is completely intercepted by light intercepting portions 36 made of chromium (Cr), as shown in FIG. 5(a). The illumination light P1 which has passed only through light transmitting portions 37 is guided to the photodiode array 31, and a circuit pattern is then imaged on the photodiode array 31 in accordance with the amplitude intensity of light. The luminous intensity distribution of a circuit pattern image at an imaging position 38 is shown in FIG. 5(b), where reference numeral 36' denotes a position of an intercepted image corresponding to the light intercepting portions 36, reference numeral 37' denotes a position of a transmitted image corresponding to the light transmitting portions 37, and reference numeral 39 denotes a luminous intensity distribution of the circuit pattern image at the imaging position 38.

In the conventional amplitude type of photomask 1, in order to enhance the detection sensitivity to slight defects in the circuit pattern 4, the light amplitude intensity of the circuit pattern image of the photomask 1 which is formed on the photodiode array 31 is heightened to the utmost. In other words, in order to heighten the resolution, the wavelength λ of the illumination light P1 with which the photomask 1 is illuminated is shortened, and the numerical aperture NA of the objective lens 30 is enlarged. This is based on the optical theory that, if illuminating conditions are fixed, the optical intensity of an image becomes larger as the value λ/NA becomes smaller.

The photomask 1 which has been regarded as having no defects in the circuit pattern 4 is attached to an exposure unit. The circuit pattern 4 is then imaged on a wafer by the illumination light P1 of the exposure unit having an objective lens with a large numerical aperture NA. However, it is unallowable to make the value λ/NA smaller than a predetermined value, for the following reason.

A resist serving as a photosensitive agent is applied to the wafer. The film thickness of the resist is 1 μm and over, as a result of considering the etching of a ground after exposure. A depth of focus equal to or larger than 1 μm is required to, with respect to the direction of the film thickness, expose the resist to light while keeping the contours of the image clear.

However, the depth of focus, the wavelength λ, and the numerical aperture NA have a relationship to each other in that the depth of focus becomes smaller in proportion to λ/(NA)². Especially, the numerical aperture NA contributes to the depth of focus by the square of the numerical aperture NA. The limited value of the depth of focus is approximately 0.6μm. Thus, the conventional exposure method is limited in enhancing the resolution of a circuit pattern image.

Consequently, the phase-shift photomask 40 (e.g., attenuated photomask) shown in FIGS. 6(a) and 6(b) has been used to obtain higher resolution than hitherto by the use of the conventional exposure unit.

The structure of the phase-shift photomask 40 will now be described.

As shown in FIG. 6(a), on a glass base, light intercepting portions 42 are formed which are made of a material having a higher refractive index than that of light transmitting portions 41. The light intercepting portions 42 transmit part of the illumination light P1. A phase of the part of the illumination light P1 which has passed through the light intercepting portions 42 is delayed with respect to that of the illumination light P1 which has passed through the light transmitting portions 41.

The phase difference between the illumination light P1 which has passed through the light transmitting portions 41 and the illumination light P1 which has passed through the light intercepting portions 42 causes interference therebetween. As a result, a circuit pattern image at the imaging position 38 is formed not only by the light amplitude intensity but also by the interference caused by the phase difference.

FIG. 6(b) shows the luminous intensity distribution of the circuit pattern image at the imaging position 38. In FIG. 6(b), reference numeral 41' denotes a transmission image position corresponding to the light transmitting portion 41, reference numeral 42' denotes an interception image position corresponding to the light intercepting portion 42, and reference numeral 43 denotes a distribution of the luminous intensity of the circuit pattern image at the imaging position 38.

According to the photomask 40, the minimum value δ of a luminous intensity distribution 43 can be made smaller than the minimum value δ' of a luminous intensity distribution 39. As a consequence, the contrast of the circuit pattern image having a wavelength equal to or shorter than the wavelength λ of the illumination light P1 can be expected to be improved. Thus, the contours of the circuit pattern image become clear. Since the resist applied to the wafer has the property of strengthening a contrast, this effect can be heightened even more.

However, in the phase-shift photomask 40, part of light can pass through the light intercepting portions 42. This makes it more difficult to detect pattern defects, such as a pin hole with a diameter below 0.35 μm, if inspection is carried out with inspection light same in wavelength as exposure light.

SUMMARY OF THE INVENTION

It is therefore an object of the present invention to provide a method of and an apparatus for inspecting slight defects in a pattern of a photomask, by which slight defects, such as a pin hole with a diameter of 0.35 μand less, can be inspected closely and with certainty.

In a method of inspecting slight defects in a pattern of a photomask according to an aspect of the present invention, the pattern whose image is projected onto an imaging position by using illumination light with an exposure wavelength for exposure comprises light transmitting portions formed on a transparent base and light intercepting portions formed on the transparent base which transmit part of the illumination light a phase of which is delayed with respect to a phase of the illumination light passing through the light transmitting portions. The method includes the step of detecting defects in the pattern on the basis of a signal obtained by illuminating the pattern with inspection light having a wavelength different from the exposure wavelength. The inspection light satisfies the formula $$T \geq (Thr-0.01)^{1/1.8}$$

where T is a transmittance of the light intercepting portion with respect to the inspection light with the inspection wavelength, and Thr is a signal detection limit of an inspection circuit, on the supposition that a signal level of the inspection light passing through the light transmitting portions is 1.

According to the present invention, a photomask is illuminated with illumination light having a longer wavelength than that of exposure light when inspection is carried out.

The phase of the illumination light which passes through light intercepting portions is delayed with respect to the phase of the illumination light which passes through light transmitting portions. When inspection is carried out using the illumination light having a longer wavelength than that of exposure light, a luminous intensity distribution of the illumination light is largely varied if slight defects in a pattern exist.

BRIEF DESCRIPTION OF THE DRAWINGS

FIG. 4(a) is a plan view of the photodiode array, and FIG. 4(b) is a perspective view of an X-Y table where the photomask is mounted.

FIG. 5(a) is a sectional view of the amplitude-type photomask, and FIG. 5(b) shows a luminous intensity distribution at an imaging position.

FIG. 6(a) is a sectional view of the phase-shift photomask, and FIG. 6(b) is a luminous intensity distribution at an imaging position.

FIGS. 9(a) to 9(h) are graphs showing the variation of a luminous intensity distribution when the size of the pattern defect is varied using illumination light which serves as inspection light and has a longer wavelength than a wavelength of exposure light.

DETAILED DESCRIPTION OF THE PREFERRED EMBODIMENTS

Figure 1:
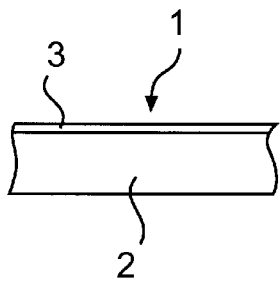
FIG. 1 is a partially sectional view of a photomask.
Figure 2:
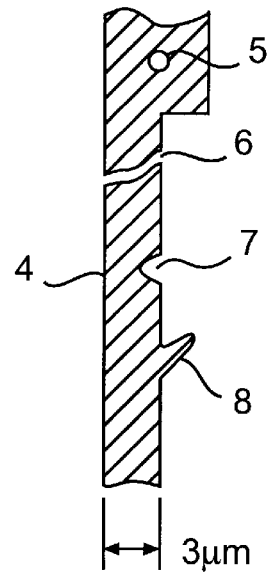
FIG. 2 is a partially enlarged view of the photomask, showing an example of defects in a circuit pattern in a chip formed in the photomask.
Figure 4A:
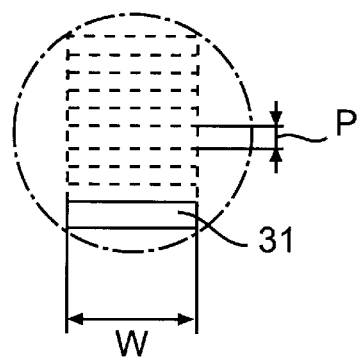
FIGS. 4(a) and 4(b) show a relationship between a photodiode array shown in FIG. 3 and the photomask.
Figure 4B:
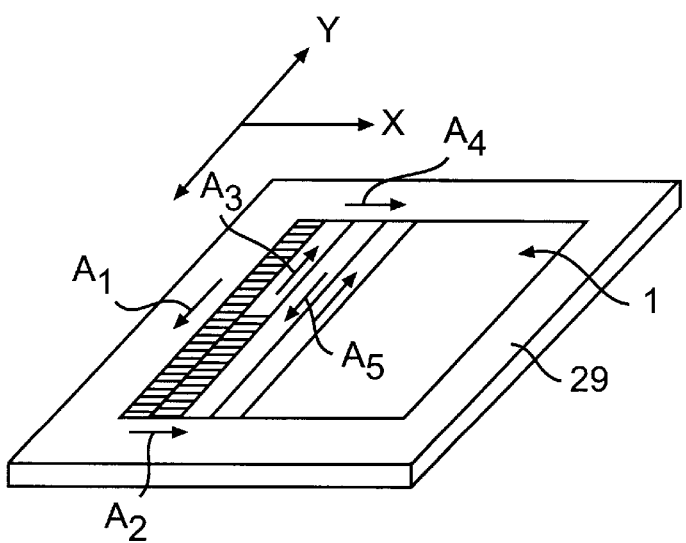
Figure 3:
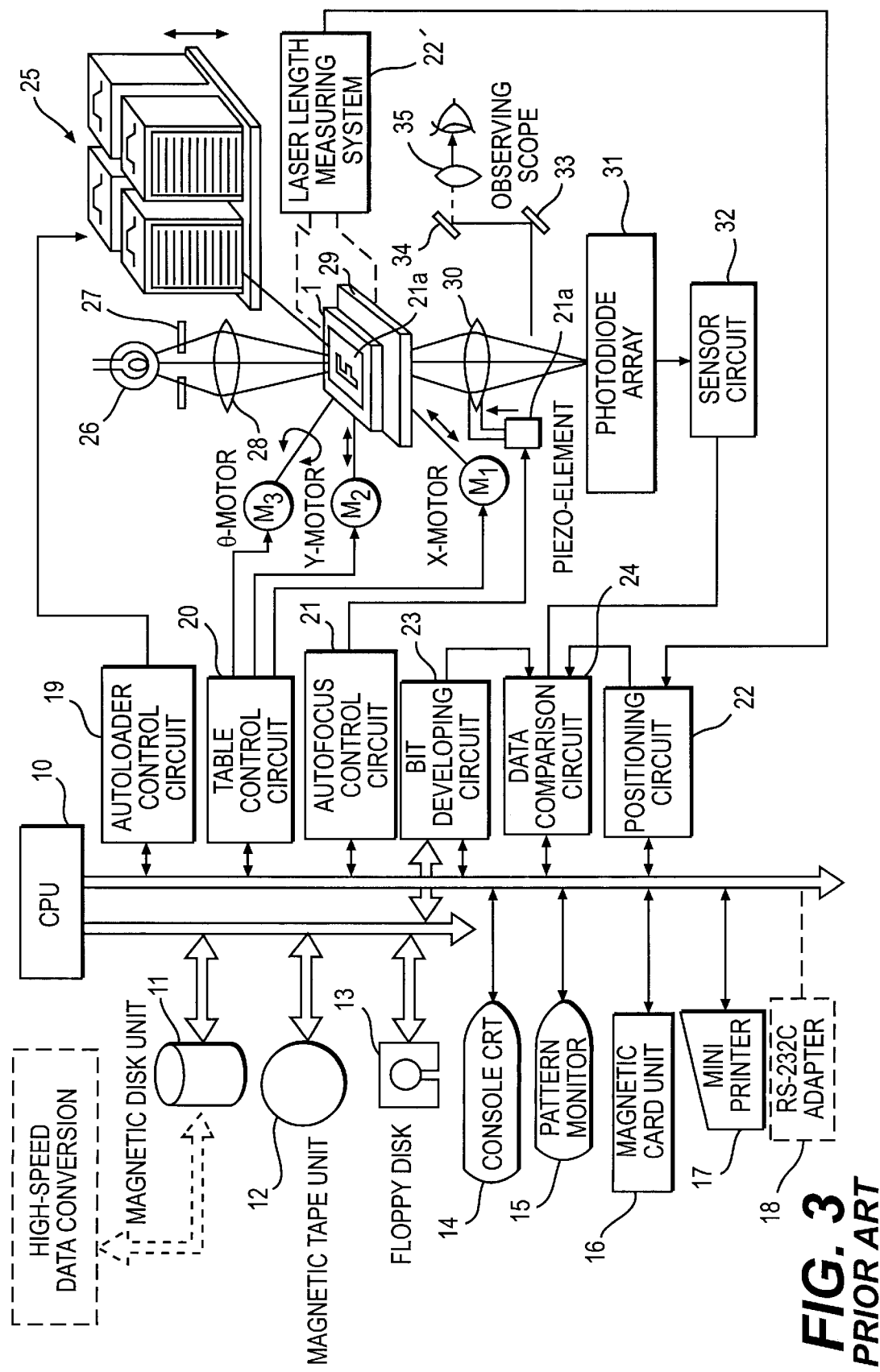
FIG. 3 is a descriptive drawing of an apparatus for inspecting defects in a pattern of a photomask.
Figure 5A:
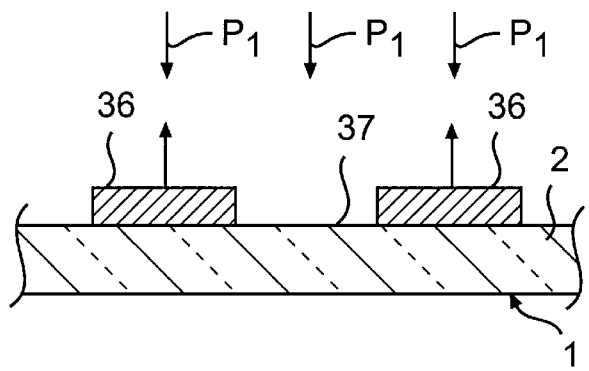
FIGS. 5(a) and 5(b) show an example of amplitude-type photomasks.
Figure 5B:
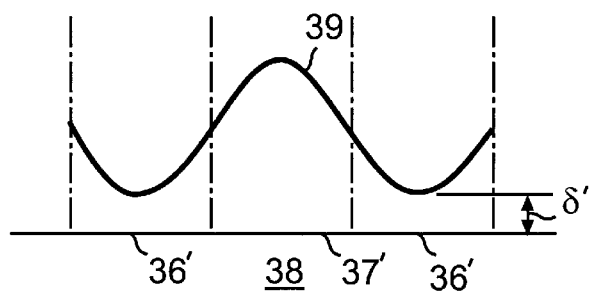
Figure 6A:
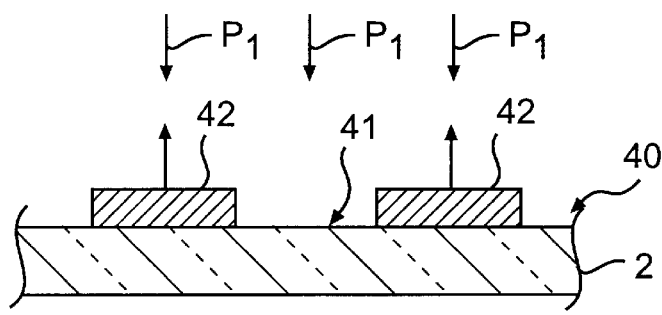
FIGS. 6(a) and 6(b) show an example of phase-shift photomasks.
Figure 6B:
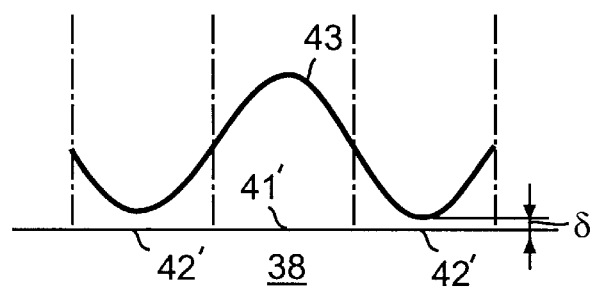

Generally, a phase-shift photomask 40 is designed to meet the following two conditions. One of them is that the transmittance of light waves in light intercepting portions 42 is 1 to 4% in a case where the wavelength of illumination light P1 for exposure is an exposure wavelength $\lambda$, and the other is that the phase or the illumination light P1 transmitted by the light intercepting portions 42 has a phase lag of $\pi$ with respect to the phase of the illumination light P1 transmitted by light transmitting portions 41. Consideration will be given to a case where defects in a circuit pattern of the phase-shift photomask 40 are inspected using a pattern defect inspection apparatus shown in FIG. 3.

The minimum dimensions of the circuit pattern of the phase-shift photomask 40 are larger than a resolution limit in a detection optical system. An image of the circuit pattern thrown on a photodiode array 31 retains the configuration of the circuit pattern.

In contrast, pattern defects, such as an extraneous substance or a flaw, are much larger and smaller in dimensions than the pattern. An image of a large pattern defect is thrown onto the photodiode array 31 while retaining the configuration corresponding to the pattern defect.

Figure 7:
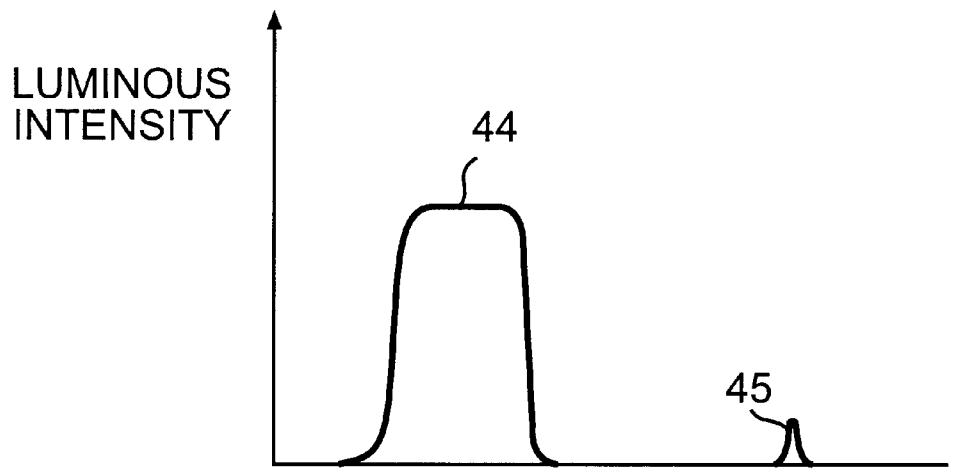
FIG. 7 is a graph showing a difference in the luminous intensity distribution depending on the size of a pattern defect.

Therefore, a luminous intensity distribution 44 (an image) becomes the configuration equivalent to the large pastern defect (see FIG. 7). When an image based on a small pattern defect becomes below the resolution limit the configuration corresponding to the small pattern defect cannot be retained. In other words, the image based on the small pattern defect becomes a spot image which is determined by the resolution in the detection optical system. Reference numeral 45 in FIG. 7 denotes a luminous intensity distribution formed by pattern defects having the dimensions smaller than the resolution limit. We will discuss not large pattern defects but small pattern defects because the large pattern defects are possible to detect with sufficient ease by the conventional pattern defect inspection method.

Figure 8:
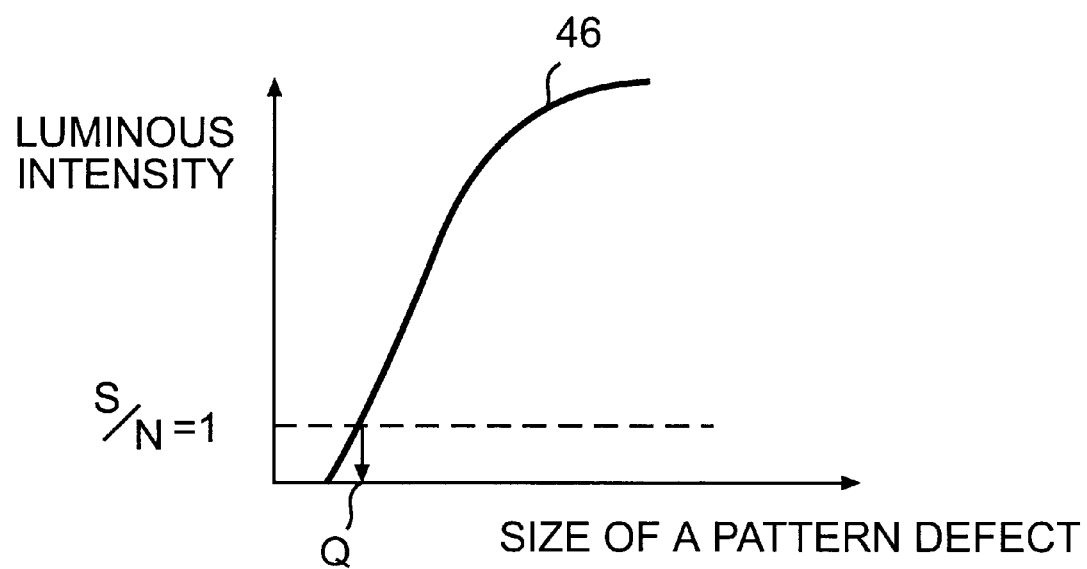
FIG. 8 is a graph showing the variation of a luminous intensity when the size of the pattern defect is varied.
Figure 9A:
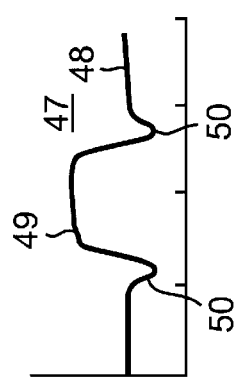
Figure 9A:
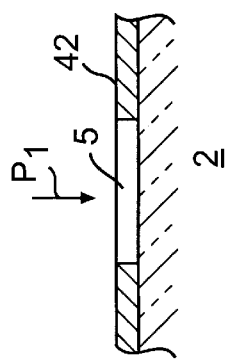
Figure 9B:
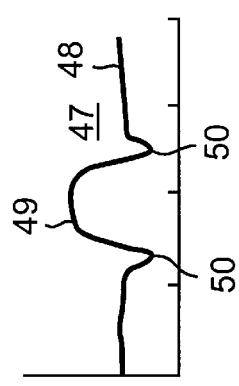
Figure 9B:
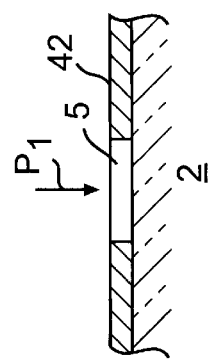
Figure 9C:
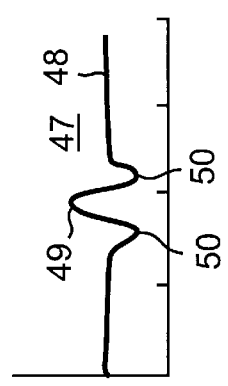
Figure 9C:
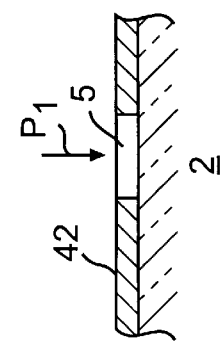
Figure 9D:
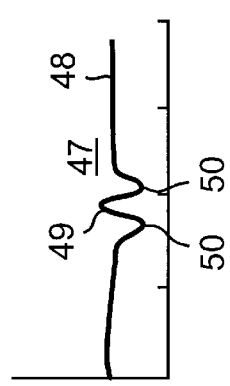
Figure 9D:
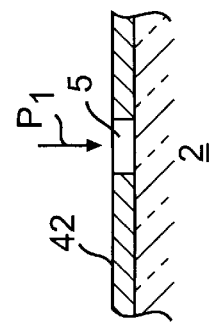

As shown in FIG. 8, the luminous intensity 46 which reaches the photodiode array 31 varies according to the size of the pattern defect. In principle, pattern defects can be detected when the luminous intensity whose value of S/N is equal to or greater than 1 reaches the photodiode array 31. Herein, the noise of the photodiode array 31 is denoted by reference character N and a photoelectric transformation signal of the light which has reached the photodiode array 31 by S. The minimum size Q of a detectable pattern defect equates with the size of a pattern defect which can obtain a luminous intensity equivalent to S/N=1.

The refractive index and transmittance of a high refractive substance out of which the light intercepting portions 42 are made are varied according to the variation of the wavelength of the illumination light P1. If an inspection wavelength $\lambda 0$ greater than the exposure wavelength $\lambda$ is selected properly, the transmittance at which the illumination light P1 used as inspection light is transmitted by the light intercepting portions 42 can be made higher than the transmittance in the exposure wavelength $\lambda$. Silicon nitride (SiN), molybdenum siliside (MoSi), silicon carbide (SiC), or the like is used as the high refractive substance out of which the light intercepting portions 42 are made. For example, the transmittance at which the illumination light P1 used as the inspection light is transmitted in the wavelength $\lambda 0$ by the light intercepting portions 42 is designed to become 50%, and the phase difference between the illumination light P1 transmitted by the light transmitting portions 41 and the illumination light P1 transmitted by the light intercepting portions 42 is designed to become $\pi$. As shown in FIGS. 9(a) to 9(h), the luminous intensity distribution 47 varies when the diameter of a pin hole 5 is successively varied. In FIGS. 9(a) to 9(h), reference numeral 48 is regarded as a luminous intensity (a base output in a case where photoelectric transformation is carried out by the photodiode array 31) obtained by the illumination light P1 which is transmitted by the light intercepting portions 42, reference numeral 49 is regarded as the luminous intensity obtained by the illumination light P1 which is transmitted mainly by the pin hole 5, and reference numeral 50 is regarded as a luminous intensity obtained by the interference between the illumination light P1 which is transmitted by the light intercepting portions 42 and the illumination light P1 which is transmitted mainly by the pin hole 5.

Figure 10:
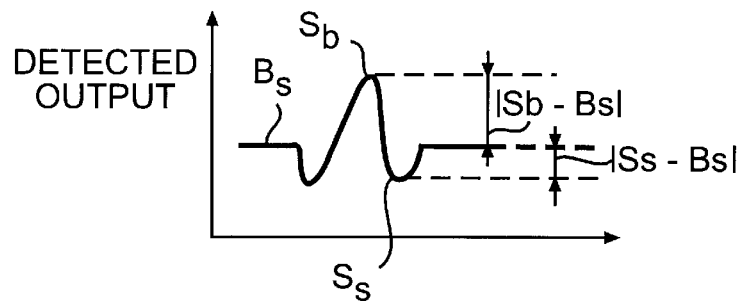
FIG. 10 is a graph showing differences in output.

As shown in FIG. 10, a base output based on the illumination light P1 which is transmitted by the light intercepting portions 42 is designated by reference character Bs, the maximum value of the detected output which is larger than the base output Bs is designated by Sb, and the minimum value of the detected output which is smaller than the base output Bs is designated by Ss. From the luminous intensity distribution 47 shown in FIGS. 9(a) to 9(h), there are calculated the absolute value |Sb-Bs| of a difference between the detected output maximum value Sb and the base output Bs in the inspection wavelength $\lambda 0$, and the absolute value |Ss-Bs| of a difference between the detected output minimum value Ss and the base output Bs in the inspection wavelength $\lambda 0$. There are also calculated the absolute value |Sb-Bs|' of a difference between the detected output maximum value Sb and the base output Bs in the exposure wavelength $\lambda$, and the absolute value |Ss-Bs|' of a difference between the detected output minimum value Ss and the base output Bs in the exposure wavelength $\lambda$. The calculation results are plotted into curved lines to obtain a graph shown in FIG. 11, wherein a solid line denotes the absolute value |Sb-Bs| of the difference between the detected output maximum value Sb and the base output Bs, and an alternate long and short dash line denotes the absolute value |Ss-Bs| of the difference between the detected output minimum value Ss and the base output Bs.

Figure 11:
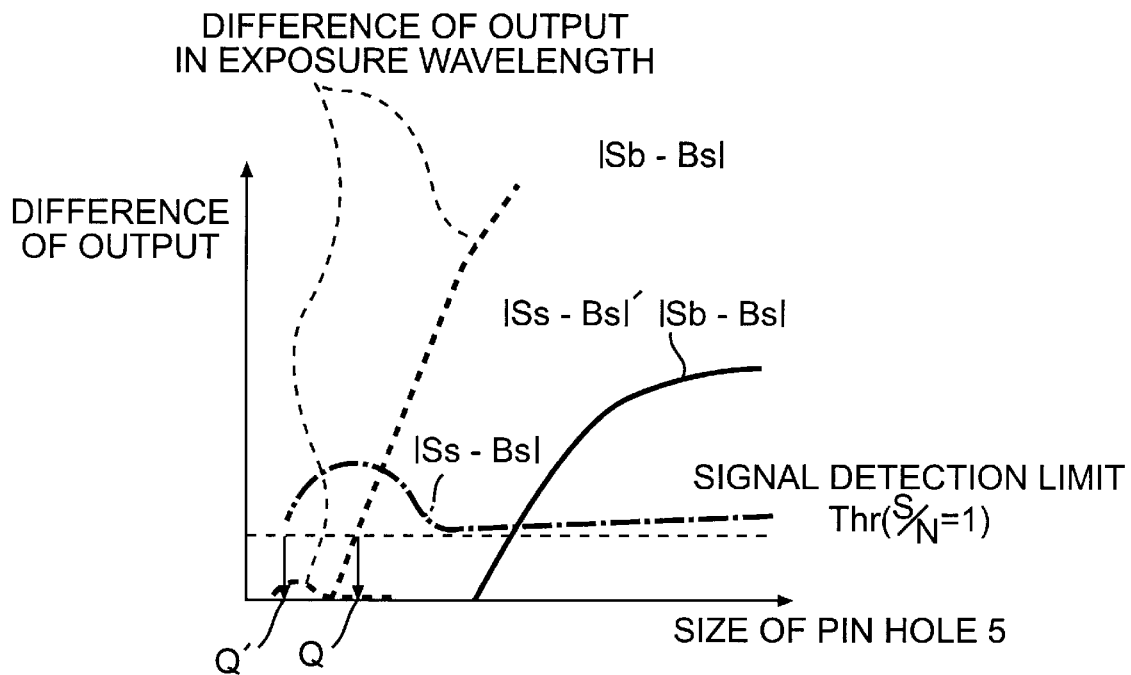
FIG. 11 is a graph showing a relationship between a difference in output and a detection limit.

Broken lines in FIG. 11 denote the absolute value |Sb-Bs|' of the difference between the detected output maximum value Sb and the base output Bs in the exposure wavelength $\lambda$, and the absolute value |Ss-Bs|' of the difference between the detected output minimum value Ss and the base output Bs in the exposure wavelength $\lambda$.

The absolute value |Sb-Bs| of the difference in the inspection wavelength $\lambda 0$ can be obtained as a much larger signal level than the absolute value |Sb-Bs|' of the difference in the exposure wavelength $\lambda$ in the range where the pin hole 5 is small in diameter. Supposing that, as shown in FIG. 11, a signal detection limit Thr is set between the absolute value |Sb-Bs| of the difference in the inspection wavelength $\lambda 0$ and the absolute value |Sb-Bs|' of the difference in the exposure wavelength $\lambda$ in a range to be measured, the diameter of the pin hole which is determined on the basis of the intersecting point between the absolute value |Sb-Bs|' in the exposure wavelength $\lambda$ and the signal detection limit Thr is equivalent to the minimum size Q of the pin hole 5 which can be detected in the exposure wavelength $\lambda$. The diameter of the pin hole which is determined on the basis of the intersecting point between the absolute value |Ss-Bs| of the difference between the detected output minimum value Ss and the base output Bs and the signal detection limit Thr is equivalent to the minimum size Q' of the pin hole 5 which can be detected in the case where the illumination light P1 having a greater wavelength $\lambda 0$ than the exposure wavelength $\lambda$ is used. Thereby, the diameter of the pin hole can be made much smaller than the minimum size Q in the exposure wavelength $\lambda$.

Hence, design data which is compared with the detected outputs is transformed into difference data in consideration of the transmittance and the phase difference in the inspection wavelength $\lambda 0$. The difference between the detected outputs is compared with the difference data by means of a data comparison circuit 24 so that slight defects of a pattern can be detected.

Consideration will now be given in more detail to the relationship between a phase difference and a transmittance of the light intercepting portions 42 in the inspection wavelength $\lambda 0$ of the illumination light P1 used for the inspection of pattern defects.

Figure 12:
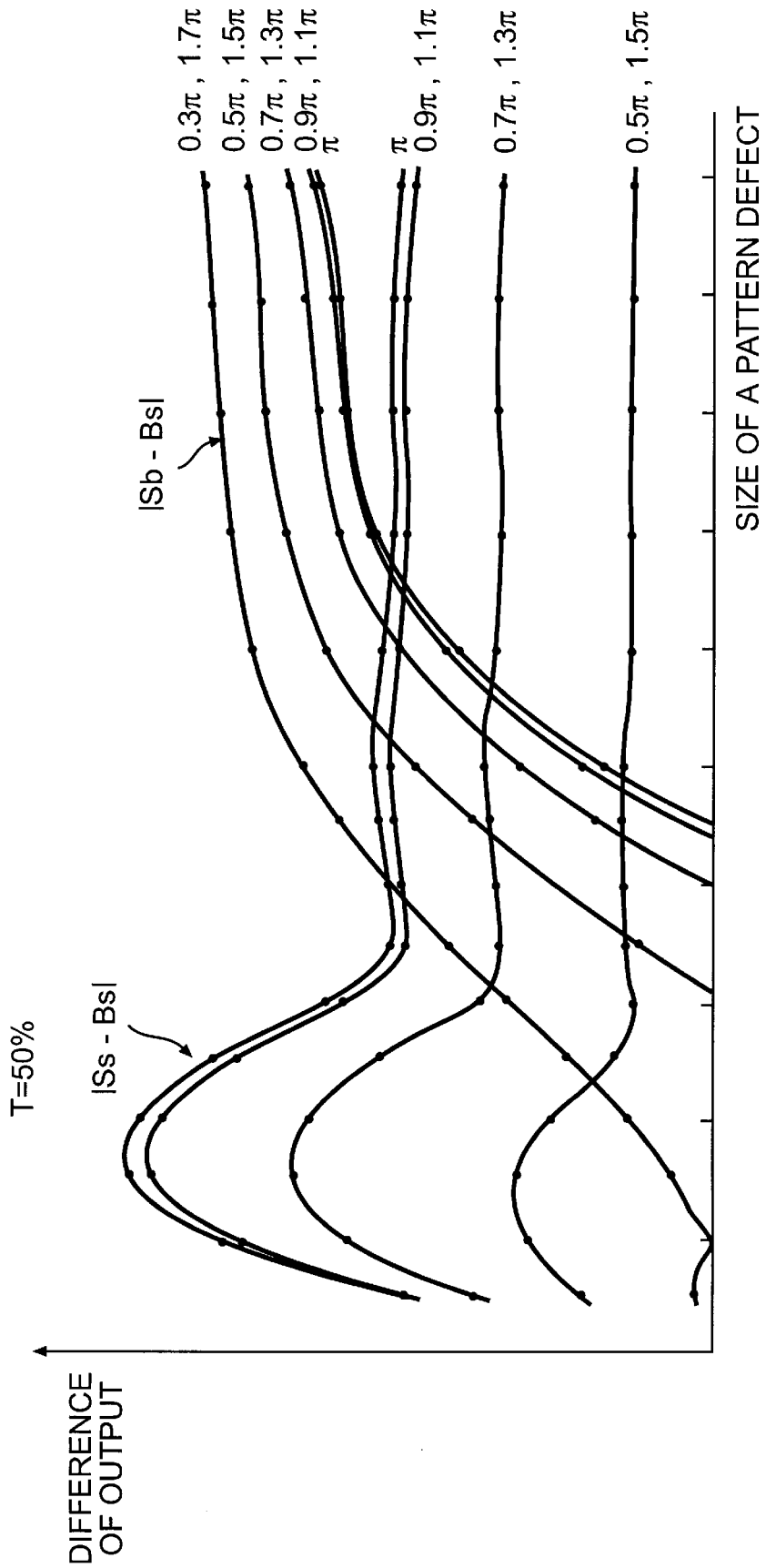
FIG. 12 is a graph shoving a relationship between the size of a pattern defect and differences in output when a transmittance of a light intercepting portion is 50%.
Figure 13:
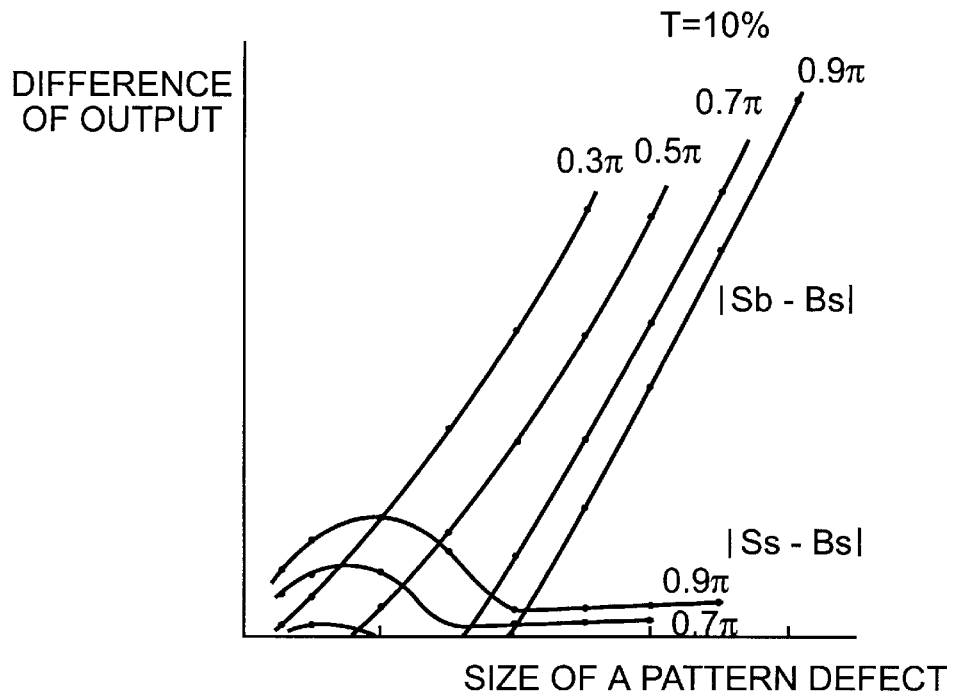
FIG. 13 is a graph showing a relationship between the size of the pattern defect and the differences in output when the phase difference is varied at intervals of 0.2 $\pi$ from 0.3$\pi$ to 0.9$\pi$ on the condition that the transmittance of the light intercepting portion is 10%.
Figure 14:
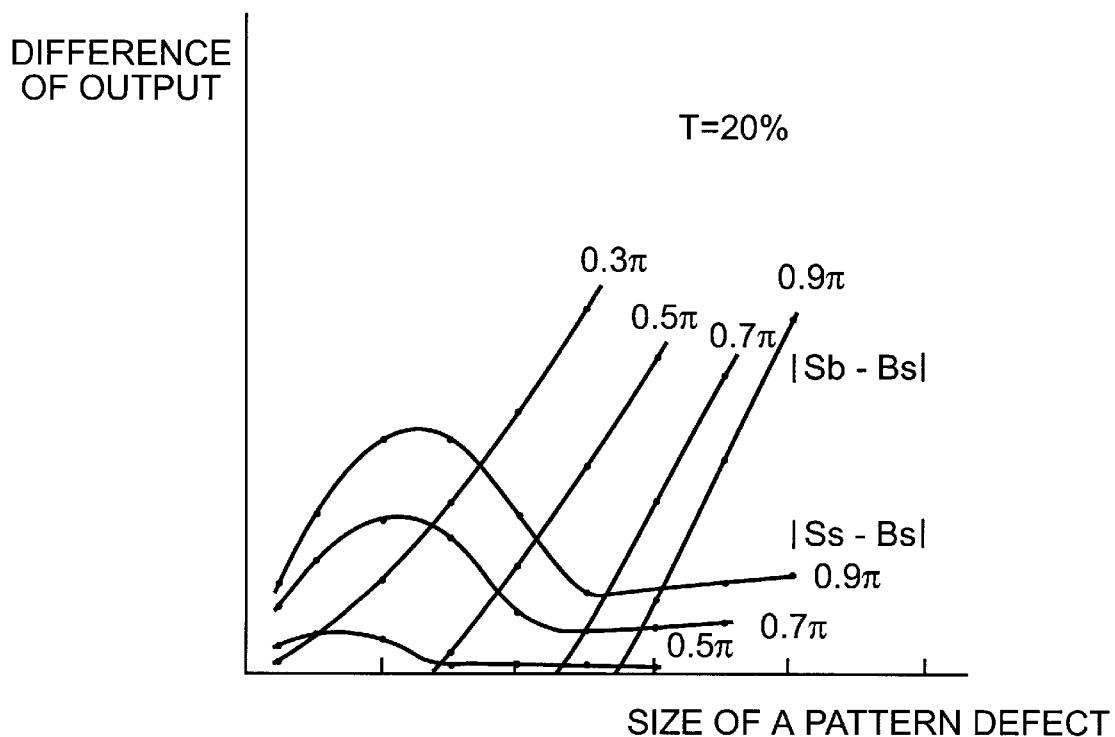
FIG. 14 is a graph showing a relationship between the size of the pattern defect and the differences in output when the phase difference is varied at intervals of 0.2$\pi$ from 0.3$\pi$ to 0.9$\pi$ on the condition that the transmittance of the light intercepting portion is 20%.
Figure 15:
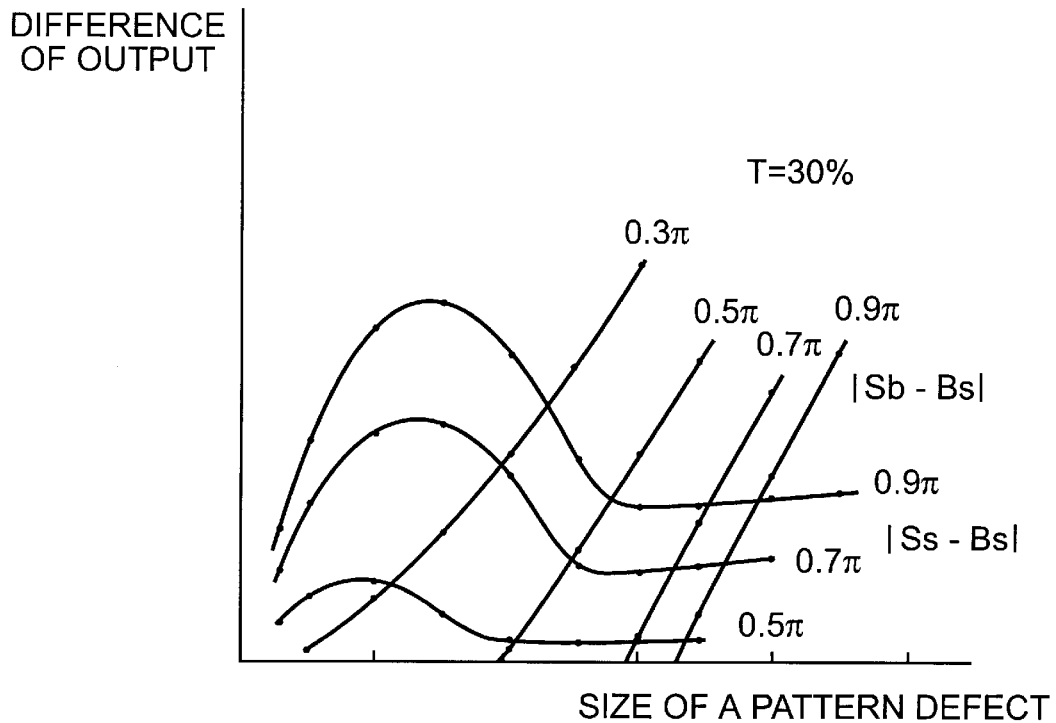
FIG. 15 is a graph showing a relationship between the size of the pattern defect and the differences in output when the phase difference is varied at intervals of 0.2$\pi$ from 0.3$\pi$ to 0.9$\pi$ on the condition that the transmittance of the light intercepting portion is 30%.
Figure 16:
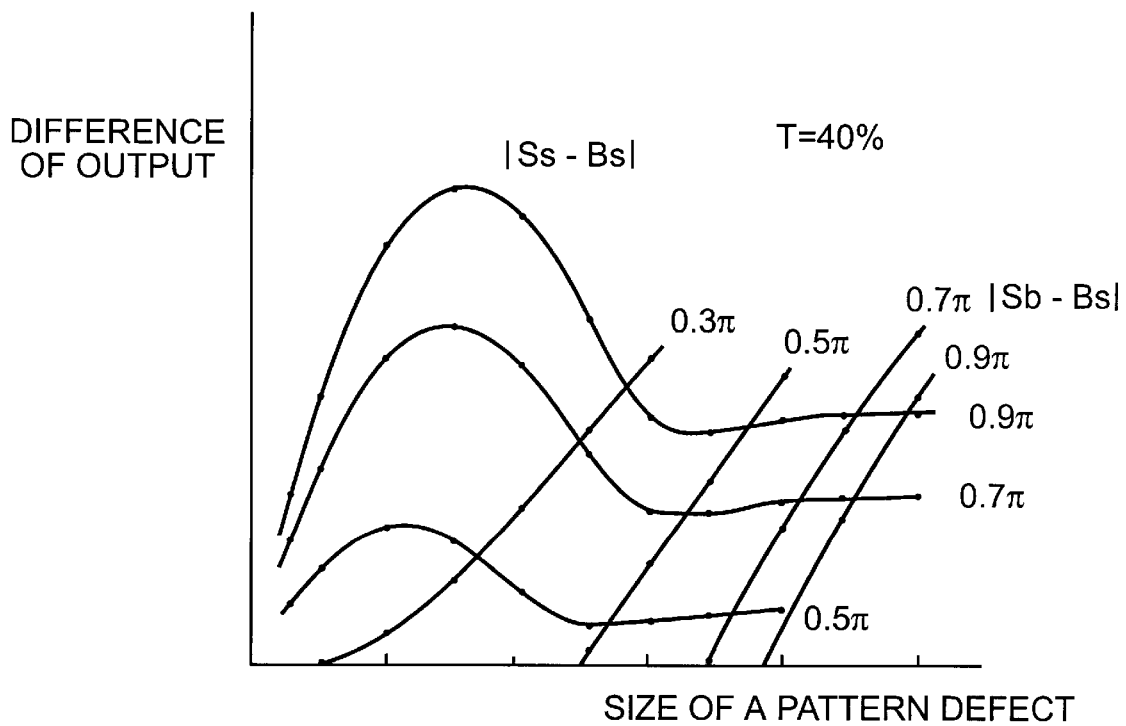
FIG. 16 is a graph showing a relationship between the size of the pattern defect and the differences in output when the phase difference is varied at intervals of 0.2$\pi$ from 0.3$\pi$ to 0.9$\pi$ on the condition that the transmittance of the light intercepting portion is 40%.
Figure 17:
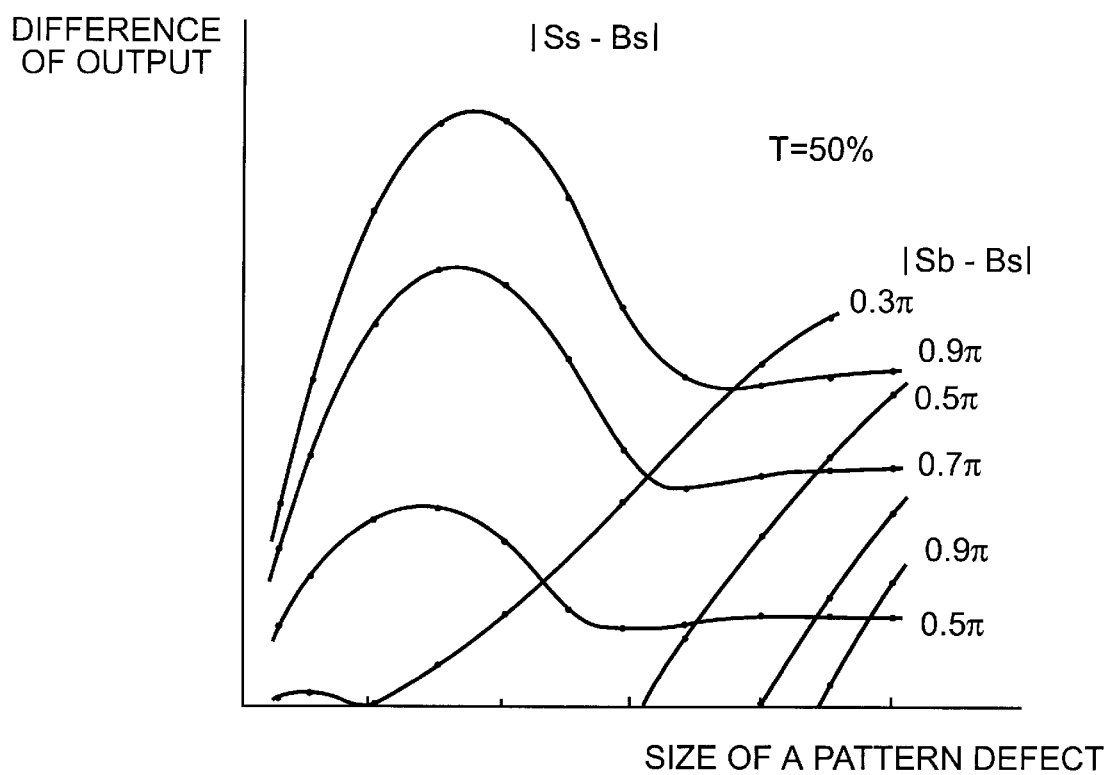
FIG. 17 is a graph showing a relationship between the size of the pattern defect and the differences in output when the phase difference is varied at intervals of 0.2$\pi$ from 0.3$\pi$ to 0.9$\pi$ on the condition that the transmittance of the light intercepting portion is 50%.
Figure 18:
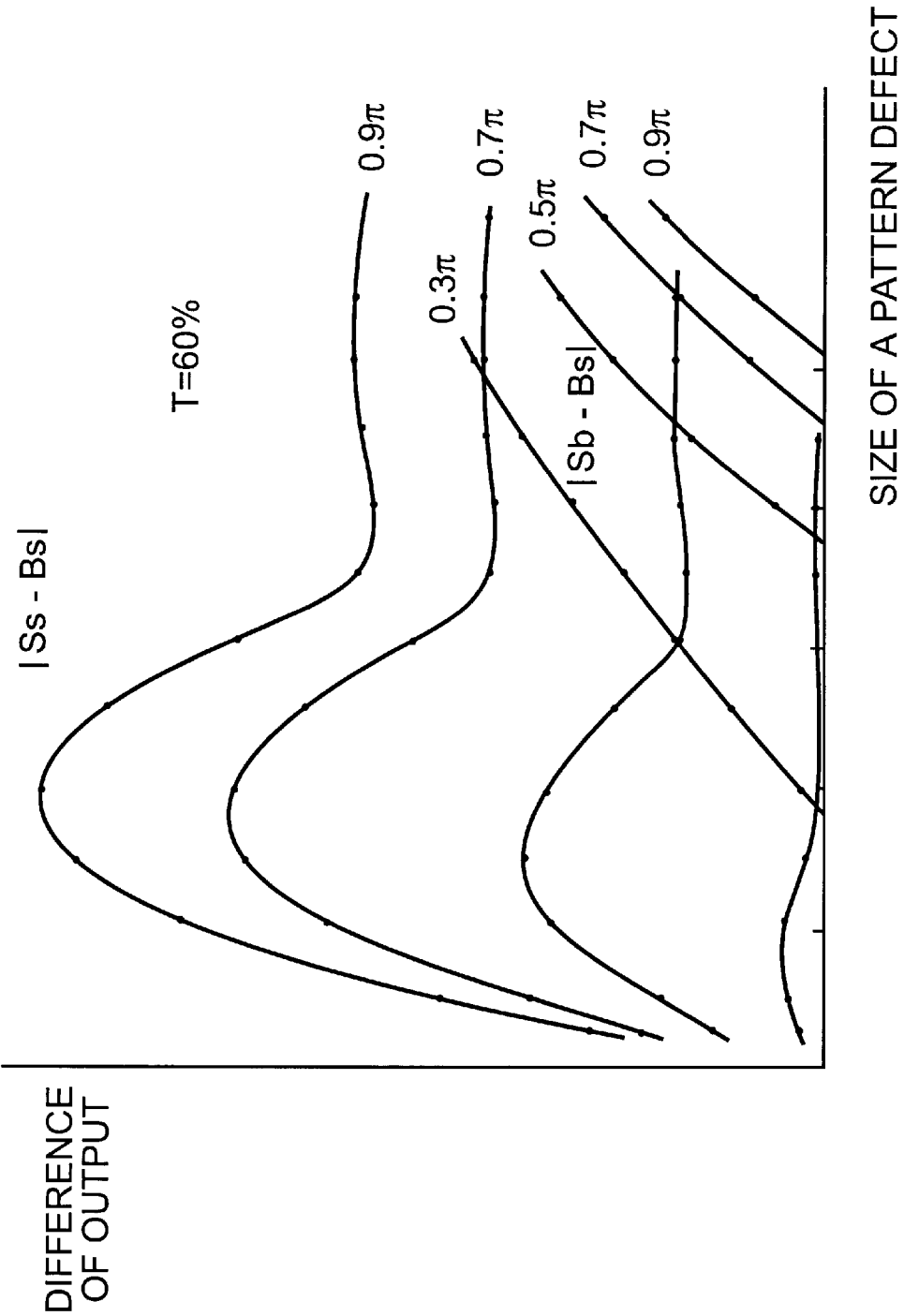
FIG. 18 is a graph showing a relationship between the size of the pattern defect and the differences in output when the phase difference is varied at intervals of 0.2$\pi$ from 0.3$\pi$ to 0.97$\pi$ on the condition that the transmittance of the light intercepting portion is 60%.
Figure 19:
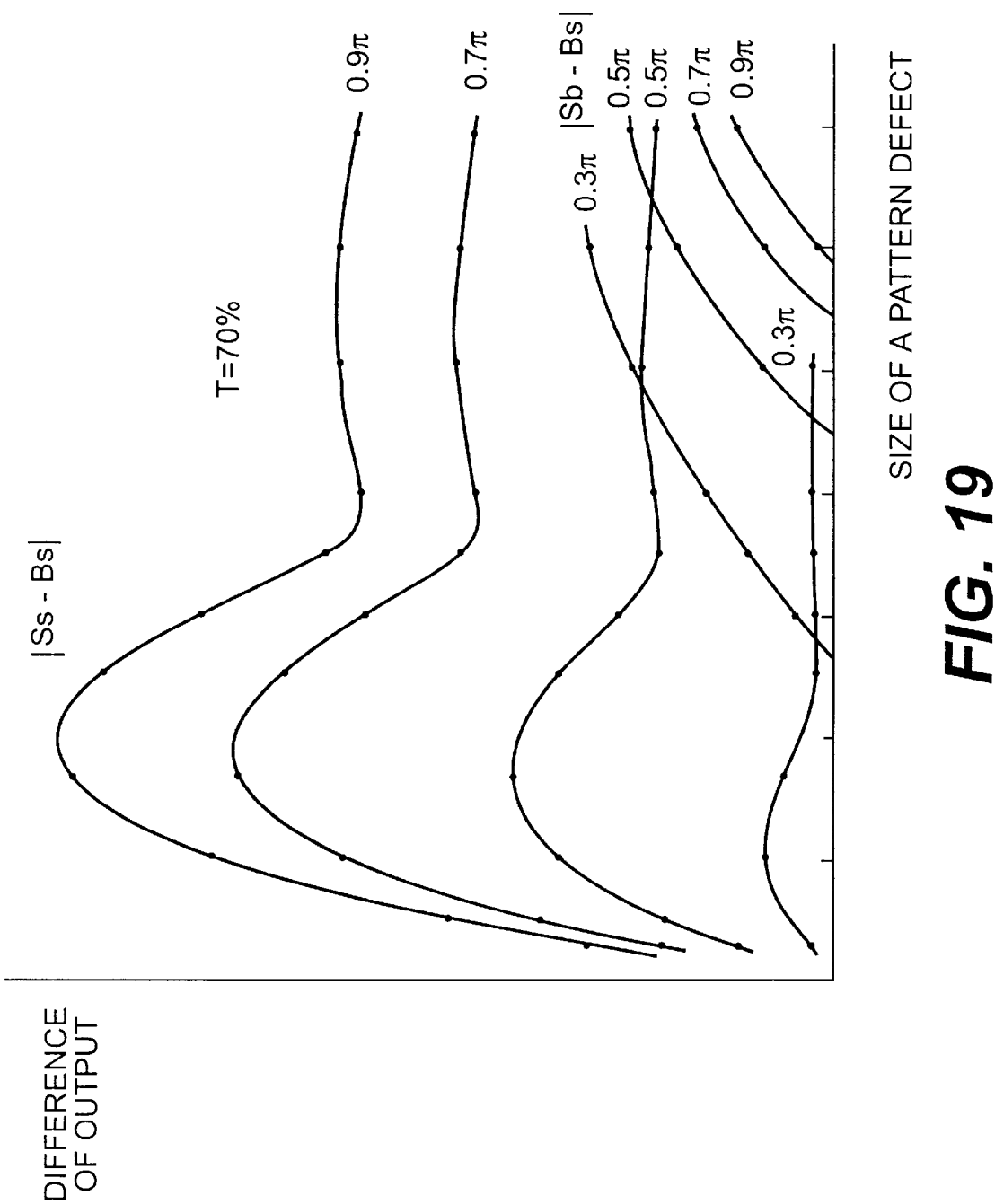
FIG. 19 is a graph showing a relationship between the size of the pattern defect and the differences in output when the phase difference is varied at intervals of 0.2$\pi$ from 0.3$\pi$ to 0.9$\pi$ on the condition that the transmittance of the light intercepting portion is 70%.

FIG. 12 is a graph showing a relationship between the differences |Sb-Bs|, |Ss-Bs| and the size of a pattern defect when the phase difference is varied from $0.3\pi$ to $1.7\pi$ on the condition that the transmittance at which the illumination light P1 is transmitted in the wavelength $\lambda 0$ by the light intercepting portions 42 is 50%. As obviously shown in FIG. 12, the differences are symmetrical about the central point of the phase difference $\pi$ (e.g., the difference at $0.3\pi$ is the same value as that at $1.7\pi$). The difference |Ss-Bs| becomes maximum at the phase difference $\pi$. Therefore, slight defects can be detected in higher probability when the phase difference is $\pi$ between the phase of the illumination light P1 which is transmitted by the light intercepting portions 42 and that of the illumination light P1 transmitted by the light transmitting portions 41.

FIGS. 13 to 19 are graphs resulting from varying the transmittance at which the illumination light P1 is transmitted in the wavelength λ0 by the light intercepting portions 42 from 10% to 70%, respectively, and plotting the differences about each of the phase differences 0.3π, 0.5π, 0.7π and 0.9π. As can be seen evidently in FIGS. 13 to 19, the higher the transmittance becomes and/or the closer the phase difference comes to π, the larger the difference |Ss−Bs| becomes and, on the other hand, the smaller the difference |Sb−Bs| becomes.

Figure 20:
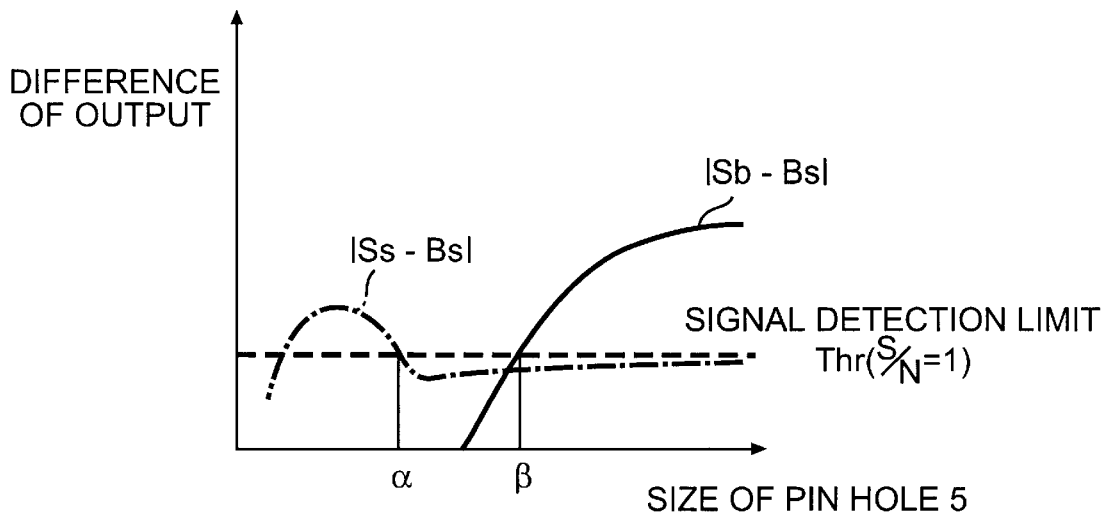
FIG. 20 is a graph showing how to ascertain whether pattern defects can be detected according to differences in output.
Figure 21:
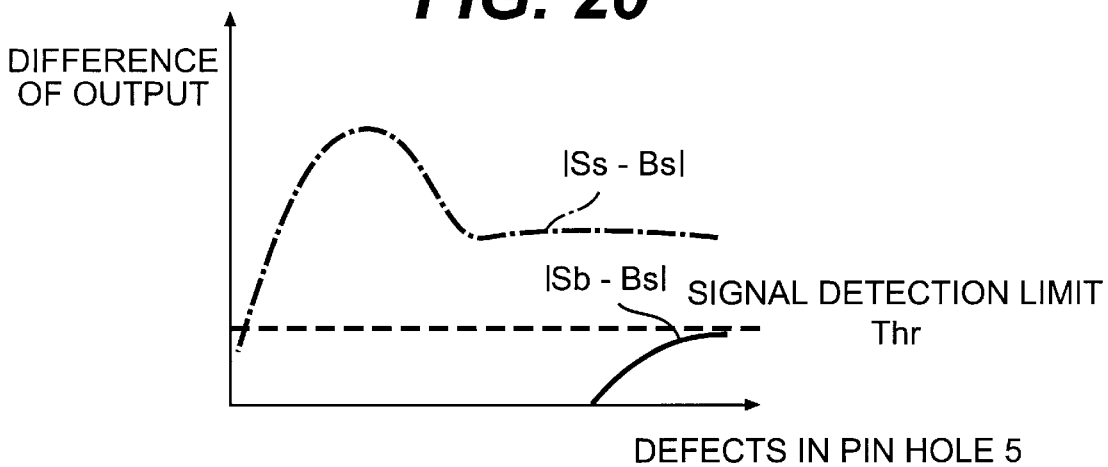
FIG. 21 is a graph showing how to ascertain whether pattern defects can be detected according to differences in output.
Figure 22:
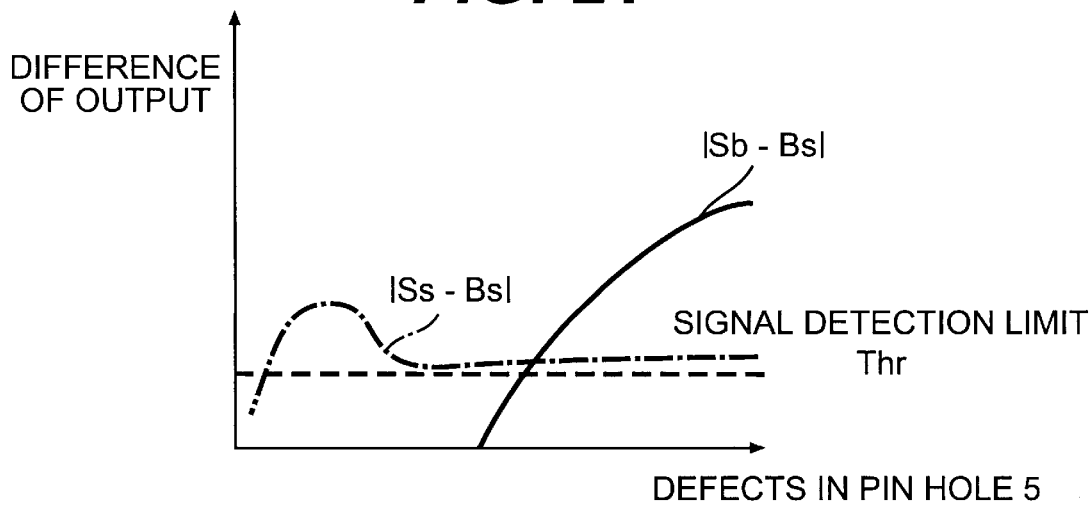
FIG. 22 is a graph showing how to ascertain whether pattern defects can be detected according to differences in output.

Thus, when the difference in output is varied by the transmittance and/or the phase difference, cases occur in which the difference |Ss−Bs| becomes equal to or less than the signal detection limit Thr in the range where the size of a slight defect is larger, depending upon the selection of the transmittance and/or the phase difference in the light intercepting portions 42, as shown in FIG. 20. In this case, the slight pattern defect cannot be detected between α and β. As shown in FIG. 21, however, the absolute value of the difference |Ss−Bs| becomes larger than the signal detection limit Thr when the transmittance in the light intercepting portions 42 is made sufficiently high. In this case, the slight pattern defect can be detected merely by using the difference |Ss−Bs|. When the difference Ss−Bs is substantially equal to the signal detection limit Thr because of the low transmittance in the light intercepting portions 42, as shown in FIG. 22, the pin hole defect can be detected by using the difference |Sb−Bs| in combination with the difference |Ss−Bs|.

Figure 23:
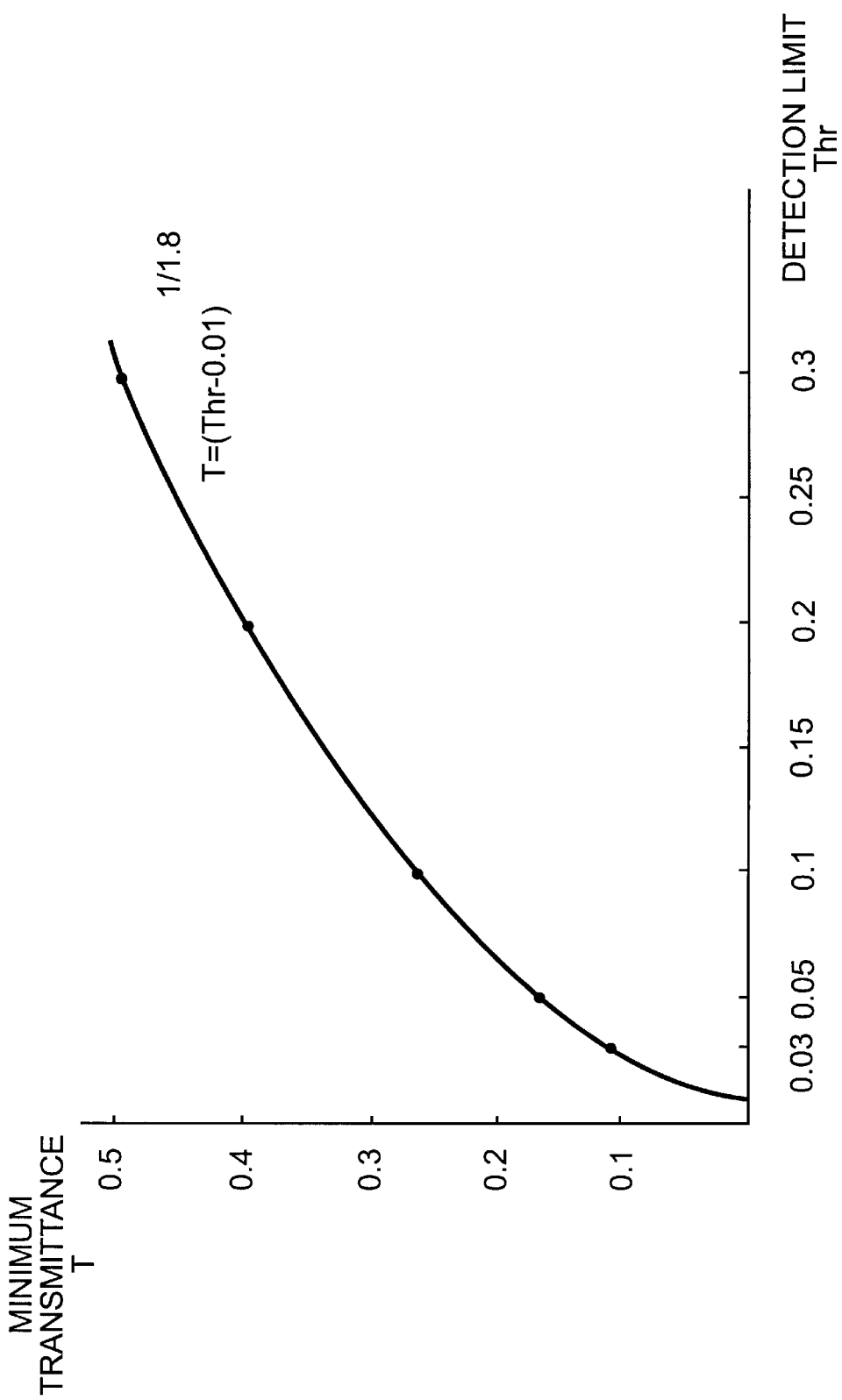
FIG. 23 is a graph showing a relationship between a signal detection limit Thr and the minimum value of the transmittance T in the light intercepting portions at which the difference |Ss−Bs| on a level with the signal detection limit Thr is obtained when the phase difference is $\pi$.

FIG. 23 shows a relationship between the signal detection limit Thr and the minimum value of the transmittance T in the light intercepting portions 42 which allows obtaining the difference |Ss−Bs| same in level as the signal detection limit Thr when the phase difference is π. A curved line in FIG. 23 is obtained from the following equation:

$$T = (Thr - 0.01)^{1/1.8}$$

Then, it is possible to detect slight defects in the pattern on the basis of a signal obtained by illuminating the pattern with inspection light having an inspection wavelength different from the exposure wavelength. The inspection light satisfies the formula $$T \geq (Thr - 0.01)^{1/1.8}$$

where T is a transmittance of the light intercepting portions with respect to the inspection light with the inspection wavelength, and Thr is a signal detection limit of an inspection circuit, on the supposition that a signal level of the inspection light passing through the light transmitting portions is 1.

As can be seen in FIG. 23, the curved line is not extended to the range where the signal detection limit Thr is larger than 0.3. The difference |Ss−Bs| does not exceed the signal detection limit Thr at a lower value than this transmittance.

The minimum values of the difference |Ss−Bs| are then calculated with respect to the respective values of the phase difference in a case where the transmittance T is varied from 10% to 100%. In Table 1 (see the following attached sheet), those calculated values are shown on the supposition that the intensity of light which reaches the photodiode array 31 is 1 when the photomask 40 is not set.

Figure 24:
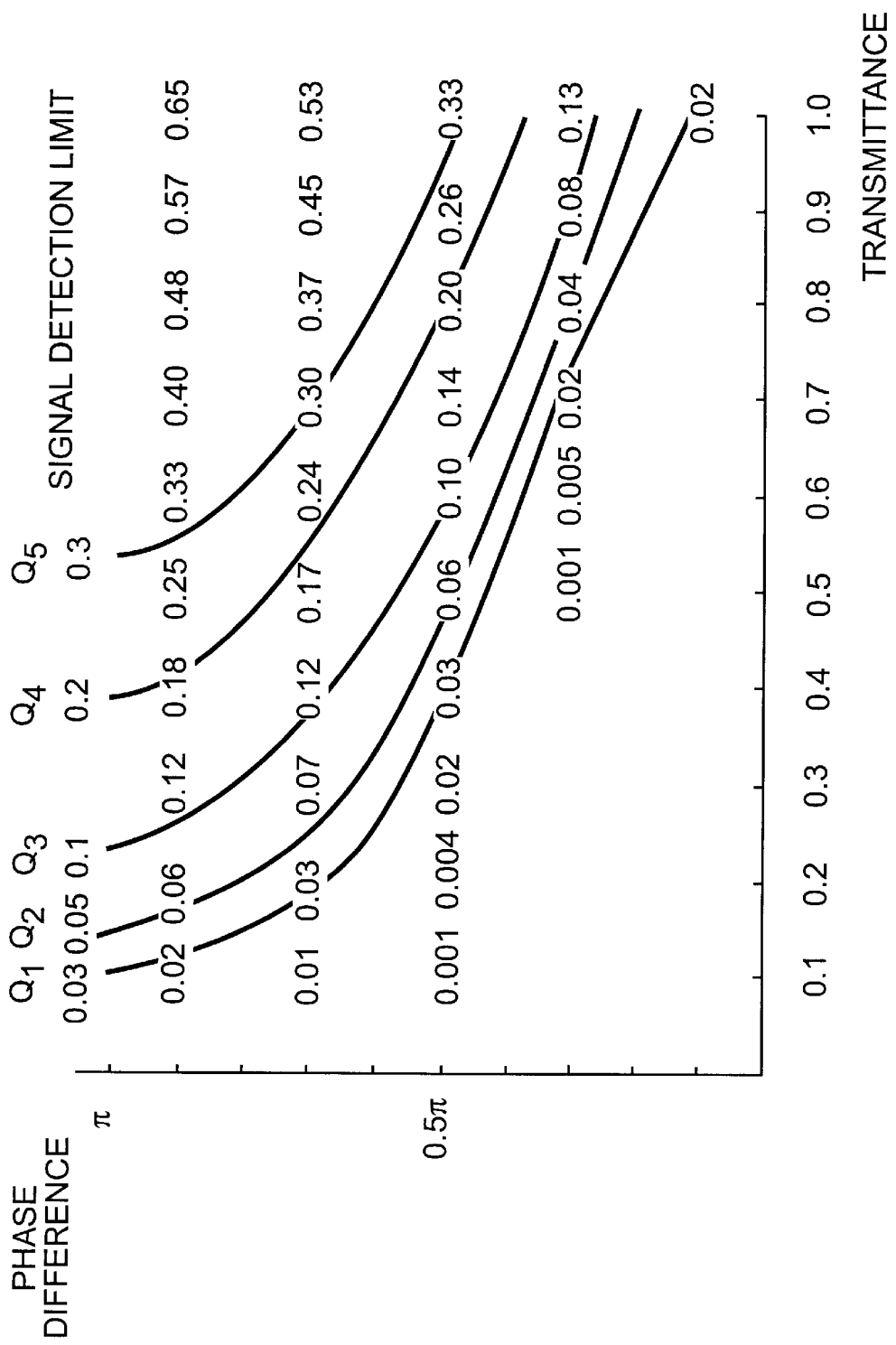
FIG. 24 is a graph showing isoplethic curves of the signal detection limit Thr which are calculated according to Table 1.

As shown in FIG. 24, isoplethic curves Q1 to Q5 of the signal detection limit Thr are obtained by plotting the values of Table 1 on a graph. In FIG. 24, the isoplethic curves Q1 to Q5 are drawn by tracing the plotted values when the signal detection limit Thr is 0.03, 0.05, 0.1, 0.2, and 0.3, respectively. The difference |Ss−Bs| can be detected in the right-side area of each of the isoplethic curves Q1 to Q5.

Figure 25:
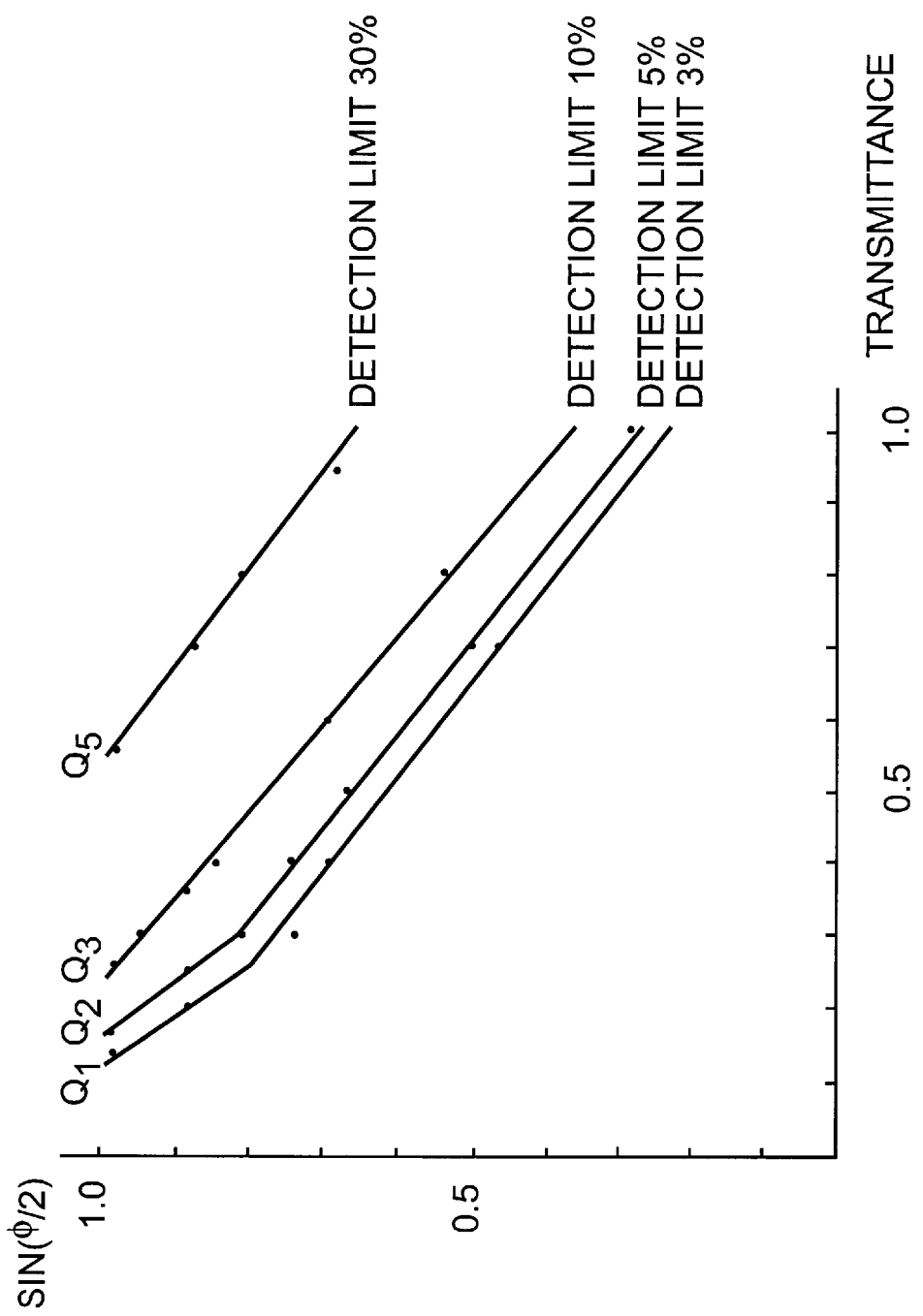
FIG. 25 is a graph showing isoplethic lines Q of the signal detection limit Thr which are obtained by transforming the phase difference $\phi$ into a sine formula.

Each line on the graph of FIG. 25 is obtained by transforming the numerical values on an ordinate axis (i.e., the phase difference φ) into values on sin (φ/2) with respect to the isoplethic curves Q1, Q2, Q3, and 5 in FIG. 24. The transmittance T iihich is obtained by transforming the phase difference φ into a sine formula becomes a linear relational expression.

From Table 1, wavelengths are selected by which the phase difference φ can satisfy the following relational expressions:

When Thr=0.03 and T<25 (%), sin (φ/2)=1.17−1.4T;

when Thr=0.03 and T≧25 (%), sin (φ/2) 1.0−0.75T;

when Thr=0.05 and T<30 (%), sin (φ/2)=1.2−1.25T;

when Thr=0.05 and T>30 (%), sin (φ/2)=1.06−0.77T;

when Thr=0.1, sin (φ/2)=1.19−0.81T; and when Thr=0.3, sin (φ/2)=1.40−0.72T.

If the phase difference obtained when the relations are solved is designated by φ the phase difference φ is between (2nπ+φm ) and (2(n+1)π−φm), wherein reference character n denotes a positive integral number or 0 (zero). If the phase difference obtained by interpolation in the transmittances is designated by φm in a case where the detection limit Thr is an intermediate value thereof, the phase difference φ is between (2nπ+φm) and (2(n+1)π−φm), wherein reference character n denotes a positive integral number or 0 (zero).

As described above, when inspecting the slight defects of the circuit pattern of the phase-shift photomask 40, use is made of inspection light having a longer wavelength than an exposure wavelength. Thereby, defects of a pin hole with the diameter below 0.35 μm can be detected with certainty. It is desirable that the photomask 40 is made of a substance whose transmittance increases in the range of the longer wavelength than the exposure wavelength λ. For example, in the photomask 40 where the i-line (having the wavelength of 365 nm) of a super-high-pressure mercury lamp is used as the exposure wavelength λ, it is preferable that slight defects of the circuit pattern are inspected by using visible rays of light. As another example, in the photomask 40 where a KrF excimer laser (having the wavelength of 249 nm) is used as the exposure wavelength, it is preferable that the i-line (having the wavelength of 365 nm) of a super-high-pressure mercury lamp is used as inspection light and that the light intercepting portions 42 are constructed by a substance which satisfies the relation shown in FIG. 23 in the wavelength range of the i-line. In addition to the two examples mentioned above, in the photomask 40 where a KrF excimer laser having the wavelength of 193 nm is used as the exposure wavelength, it is preferable that the KrF excimer laser having the wavelength of 249 nm is used as inspection light and that the light intercepting portions 42 are constructed by a substance which satisfies the relation shown in FIG. 23 in the wavelength range of the KrF excimer laser having the wavelength of 249 nm.

Since this invention is constructed as described above, slight defects in the circuit pattern of the phase-shift photomask, namely, defects of a pin hole with the diameter of 0.35 μm or less can be detected without fail.

According to this method of inspecting slight defects of the photomask 40, a pattern defect inspecting apparatus can be developed which can cope with the correction of chromatic aberration and a heightened numerical aperture (N.A.), from the point of view of optical materials, if use is made of the i-line (having the wavelength of 365 nm) of a super-high-pressure mercury lamp as the inspection wavelength λ0 of inspection light.

In the embodiment mentioned above, there was described the method in which pattern defects are inspected by using the absolute value of the difference |Ss−Bs|. However, this invention is not limited to this method.

For example, an output of the photodiode array 31 is differentiated and, based on the differentiation result, pattern defects are inspected. In this case, a differentiation value Δn in the n-th position ("th" is a suffix designating an ordinal number) of the photodiode array 31 is obtained from the following equation:

Differentiation value $\Delta n = (S(n+1) - S(n-1))/d$ where S(n+1) is an output in the (n+1)-th position of the photodiode array 31, S(n−1) is an output in the (n−1)-th position thereof, and d is a pitch between picture elements. In other words, based on a difference between output values before and after a picture element, a differentiation value in its intermediate position is calculated.

A method of obtaining a differentiation value Δn is not limited to the above-mentioned method. Another method can be adopted, of course.

If the adjacent-pattern comparison method is used as the pattern defect inspection method, pattern defects can be inspected by comparing a signal obtained from a circuit pattern to be inspected with a signal obtained in a circuit pattern adjacent thereto.

Further, if the design-data comparison method is used as the pattern defect inspection method, a basic signal is generated and stored which is obtained when an ideal circuit pattern is illuminated with inspection light having a wavelength different from that of exposure light, and thereafter pattern defects can be inspected by comparing a signal obtained from the circuit pattern to be inspected with the basic signal.

mitting portions formed on a transparent base and light intercepting portions formed on the transparent base which transmit part of the exposure light a phase of which is delayed with respect to a phase of the illumination light passing through said light transmitting portions, said apparatus comprising:

an X-Y table for supporting said photomask;

an illumination light source radiating inspection light having an inspection wavelength different from the exposure wavelength onto said photomask;

means for detecting defects in said pattern based on a signal obtained by illuminating said pattern with said inspection light, said inspection light satisfying the relational expression $T \geq (Thr - 0.01)^{1/1.8}$ where T is a transmittance of said light intercepting portions with respect to said inspection light with the inspection wavelength, and Thr is a signal detection limit of an inspection circuit, given that a signal level of said inspection light passing through said light transmitting portions is 1.

2. The apparatus of claim 1, wherein the inspection wavelength of said inspection light is longer than the exposure wavelength of said exposure light.

3. The apparatus of claim 1, wherein a phase difference φ between a phase of said inspection light passing through said light transmitting portions and a phase of said inspection light passing through said light intercepting portions is selected to, in accordance with the transmittance T of said light intercepting portions and the signal detection limit Thr, satisfy the following relational expression:

$(2n\pi + \phi m) \leq \phi \leq (2(n+1)\pi - \phi m)$ where n is a positive integer number including zero (0), and φm is a phase difference obtained by solving the following equations:

$\sin(\phi/2) = 1.17 - 1.4T$ when Thr=0.03 and T<25%;

$\sin(\phi/2) = 1.0 - 0.75T$ when Thr=0.03 and T≧25%;

$\sin(\phi/2) = 1.2 - 1.25T$ when Thr=0.05 and T<30%;

$\sin(\phi/2) = 1.06 - 0.77T$ when Thr=0.05 and T≧30%;

$\sin(\phi/2) = 1.19 - 0.81T$ when Thr=0.1; and $\sin(\phi/2) = 1.40 - 0.72T$ when Thr=0.3;

TABLE 1

| | TRANSMITTANCE T (%) PHASE DIFFERENCE φ | | | | | | | | | |
|---|---|---|---|---|---|---|---|---|---|---|
| | 10 | 20 | 30 | 40 | 50 | 60 | 70 | 80 | 90 | 100 |
| 0.9 n | 0.02 | 0.06 | 0.12 | 0.18 | 0.25 | 0.33 | 0.40 | 0.48 | 0.57 | 0.65 |
| 0.7 n | 0.01 | 0.03 | 0.07 | 0.12 | 0.17 | 0.24 | 0.30 | 0.37 | 0.45 | 0.53 |
| 0.5 n | 0.001 | 0.004 | 0.02 | 0.03 | 0.06 | 0.10 | 0.14 | 0.20 | 0.26 | 0.33 |
| 0.3 n | — | — | — | — | 0.001 | 0.005 | 0.02 | 0.04 | 0.08 | 0.13 |
| 0.1 n | — | — | — | — | — | — | — | — | — | 0.02 |

What is claimed is:

1. An apparatus for inspecting slight defects in a pattern of a photomask, an image of said pattern being projected onto an imaging position by using exposure light with an exposure wavelength, said pattern comprising light transor $(2n\pi + \phi m) \leq \phi \leq (2(n+1)\pi - \phi m)$ where n is a positive integer number including zero (0), and φ m is a phase difference obtained by interpolation of the transmittances if the signal detection limit Thr is an intermediate value thereof.

4. The apparatus of claim 1, further comprising means for detecting defects from a difference in output of a signal obtained from the photomask by means of the inspection light.

5. The apparatus of claim 1, further comprising means for obtaining a differential output of a signal obtained from the photomask by means of the inspection light and for detecting defects in said pattern based on said differential output.

6. The apparatus of claim 1, further comprising means for detecting defects by comparing a signal obtained from a circuit pattern, which is an object to be inspected on the photomask by means of the inspection light, with a signal obtained from a circuit pattern adjacent to said circuit pattern by means of the inspection light.

7. The apparatus of claim 1, further comprising means for detecting defects by comparing a signal obtained from a circuit pattern, which is an object to be inspected on the photomask by means of the inspection light, with a reference signal memorized in advance, said reference signal being obtained when an ideal photomask is illuminated with the inspection light.

8. The apparatus of claim 1, wherein said inspection wavelength is i-line of a super-high-pressure mercury lamp.

* * * * *